United States Patent [19]

Yabe et al.

[11] Patent Number: 4,868,644
[45] Date of Patent: Sep. 19, 1989

[54] ELECTRONIC ENDOSCOPE WITH SOLID STATE IMAGING DEVICE

[75] Inventor: Hisao Yabe, Hachioji, Japan

[73] Assignee: Olympus Optical Co., Tokyo, Japan

[21] Appl. No.: 176,136

[22] Filed: Mar. 31, 1988

[30] Foreign Application Priority Data

Apr. 1, 1987 [JP] Japan .................................. 62-81675
May 12, 1987 [JP] Japan ................................ 62-116620

[51] Int. Cl.[4] .......................... H04N 7/18; A61B 1/06
[52] U.S. Cl. ............................................. 358/98; 128/6
[58] Field of Search ..................... 358/98, 229; 128/4, 128/6

[56] References Cited

U.S. PATENT DOCUMENTS 4,491,865 1/1985 Danna et al. .
4,573,450 3/1986 Arakawa ........................... 358/92 X
4,641,635 2/1987 Yabe .
4,741,327 5/1988 Yabe ................................. 358/98 X

FOREIGN PATENT DOCUMENTS 61-47921 3/1986 Japan .
61-182702 11/1986 Japan .

Primary Examiner—James J. Groody
Assistant Examiner—Victor R. Kostak
Attorney, Agent, or Firm—Armstrong, Nikaido, Marmelstein, Kubovcik & Murray

[57] ABSTRACT

This electronic endoscope has an insertable part having an observing window on the side of a tip part extended forward of the insertable part. The solid state imaging device is to receive an entering light from the above mentioned observing window and is arranged so as to intersect substantially at right angles with the axial direction of the above mentioned insertable part. Contents are arranged on the opposite observing window side of this solid state imaging device. This solid state imaging device is provided with wire bonding parts on the side different from the side on which the above mentioned contents are arranged.

10 Claims, 11 Drawing Sheets 4,868,644

ELECTRONIC ENDOSCOPE WITH SOLID STATE IMAGING DEVICE

FIELD OF THE INVENTION

This invention relates to an electronic endoscope wherein a solid state imaging device is provided as an imaging means and the insertable part in which this imaging device is arranged can be made small in the diameter.

BACKGROUND OF THE INVENTION

Recently, there are suggested various electronic endoscopes wherein such solid state imaging device as a charge coupled device (CCD) is used as an imaging means.

Such electronic endoscope has advantages that it is higher in resolution than a fiber scope, that it is easier to record and reproduce picture images and that such picture image processes as the magnification of picture images and comparison of two pictures are easier.

Now, conventionally, there are side viewing type electronic endoscopes wherein, as shown in the gazette, for example, of a Japanese patent application laid open No. 47921/1986, an illuminating window and observing window are provided on the side surface of the tip part of the insertable part and a solid state imaging device is arranged to interest substantially at right angles with the axial direction of the insertable part on the base side more than this illuminating window and observing window or a solid state imaging device is arranged to interest substantially at right angles with the axial direction of the insertable part on the tip side more than the above mentioned illuminating window and observing window.

This side viewing type electronic endoscope having a forceps channel is divided into two parts in a plane including the axial center line of the tip part, a forceps raising stand, forceps channel and raising wire are provided on one side half and therefore it is unavoidable that the other contents concentrate on the other half. Therefore, in order to make the diameter small, it is important to arrange the above mentioned contents at a high space efficiency.

In the solid state imaging device arranged on the base side, the illuminating window is provided on the tip side more than the observing window and the light guide of fibers is passed through the side (the side reverse to the observing window) below the solid state imaging device to make the diameter small.

Also, in the solid state imaging device arranged on the tip side, the observing window is provided on the tip side more than the illuminating window and the cable connected to the solid state imaging device is returned to the lower side (the side reverse to the observing window) of the solid state imaging device and is inserted to make the diameter small.

The electronic endoscope requires not only a solid state imaging device but also peripheral circuits for amplifying video output signals from the solid state imaging device and for forming solid state imaging device driving pulses. Signal cables electrically connecting solid state imaging apparatus including these peripheral circuits with a camera control unit for processing signals are required to be about 12 in the case of the most general four-phase driving type CCD. It is preferable to use shielding wires for these signal cables to prevent noises. Therefore, the diameter of one signal cable will become large and a considerable space will be required for wiring signal cables.

On the other hand, about 14 bonding wires for electrically connecting a solid state imaging device chip with a solid state imaging device package base are required for a four-phase driving type CCD. The space for the wire bonding is required to be about 3 mm×1 mm from the pitch of the above mentioned bonding wires and the space for providing bonding pads. This size is required to make the diameter small. This size is an inneglibible size as of an endoscope in which the diameter is required to be small and, for example, the outside diameter of the insertable part is about 10 mm for the upper or lower digestive organ.

However, where the wire bonding part occupying such large space is to be provided to make the diameter smallest has not been considered. Therefore, the diameter of the insertable part has not yet been made small enough in the arrangement of the solid state imaging device either on the base side or on the tip side.

OBJECT AND SUMMARY OF THE INVENTION

An object of the present invention is to provide an electronic endoscope wherein the wire bonding parts of a solid state imaging device are arranged at a high space efficiency so that the insertable part may be made smaller in the diameter.

In the electronic endoscope of the present invention, a solid state imaging device as an imaging means is provided in the tip part of the insertable part which is to be inserted into a body cavity. An observing window and illuminating light window are provided on the side of the tip part of the insertable part. The solid state imaging device is provided so as to intersect substantially at right angles with the axial direction of the insertable part. Contents are arranged on the opposite observing window side. The wire bonding parts of the solid state imaging device are provided on the side different from the side on which the contents are arranged.

The other features and advantages of the present invention will become apparent enough with the following explanation.

BRIEF DESCRIPTION OF THE DRAWINGS

FIG. 1 is an explanatory view showing a cross-section of the tip part of an insertable part.

FIG. 2 is an explanatory view showing a longitudinal section of the tip part of the insertable part.

FIG. 3 is n explanatory view showing a cross-section on line A—A' in FIG. 2.

FIG. 4 is a plan view of the tip part of the insertable part.

FIG. 5 is a side view showing an entire electronic endoscope apparatus.

FIG. 6 is an explanatory view showing a cross-section of the tip part of an insertable part.

FIG. 7 is a plan view of the tip part of the insertable part.

FIG. 8 is an explanatory view showing a cross-section of the tip part of an insertable part.

FIG. 9 is an explanatory view showing a cross-section of the tip part of the insertable part.

FIG. 10 is an explanatory view showing a cross-section on line D—D' in FIG. 2.

FIG. 11 is a plan view of the tip part of the insertable part.

FIG. 12 is an explanatory view showing the connection of a solid state imaging device with signal cables.

FIG. 13 is an explanatory view showing a cross-section of the tip part of an insertable part.

FIG. 14 is an explanatory view showing a longitudinal section of the tip part of the insertable part.

FIG. 15 is a plan view of the tip part of the insertable part.

FIG. 16 is an explanatory view showing a longitudinal section of the tip part of the insertable part.

FIG. 17 is a side view showing the entire endoscope apparatus with the operating part as held with a left hand.

FIG. 18 is an explanatory view showing the operating part as held with a right hand.

FIG. 19 is a perspective view showing the operating part.

FIG. 20 is a perspective view showing the operating part as rotated by 180 degrees with the center axis of the operating part as a center with respect to FIG. 19.

FIG. 21 is a sectioned view showing a switch part at the rear end of the operating part.

FIG. 22 is a perspective view showing the vicinity of the operating part.

FIG. 23 is a perspective view showing the vicinity of the operating part as rotated by 180 degrees with the center axis of the operating part as a center with respect to FIG. 22.

DETAILED DESCRIPTION OF PREFERRED EMBODIMENTS

Embodiments of the present invention shall be explained in the following with reference to the drawings:

FIGS. 1 to 5 show the first embodiment of the present invention.

Figure 5:
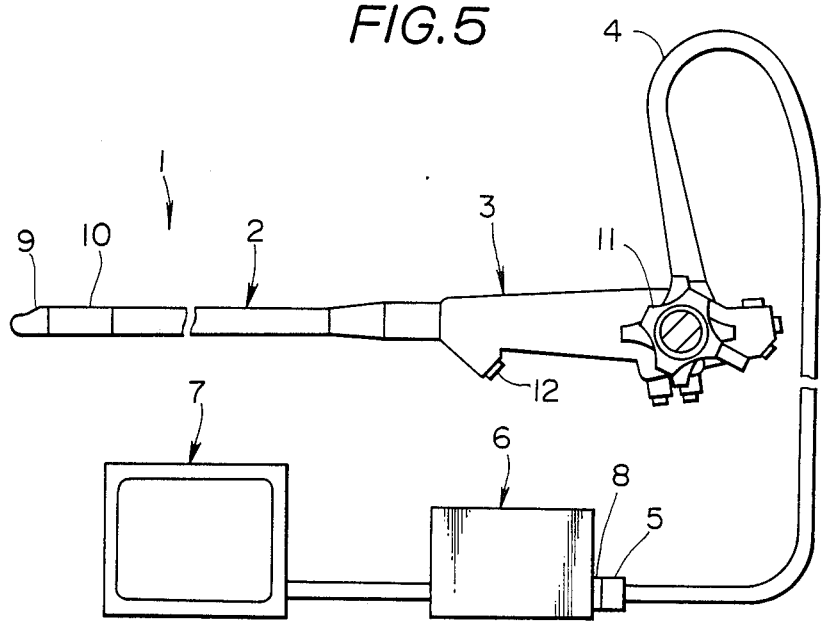

As shown in FIG. 5, in a side viewing type electronic endoscope 1 a thick operating part 3 is connected to the rear end of an elongate and, for example, flexible insertable part 2. A flexible universal cord 4 is extended sidewise from the rear end part of the above mentioned operating part 3 and is provided with a connector 5 in the tip part. On the other hand, a control apparatus 6 containing a light source apparatus and signal processing circuit is provided with a connector receptacle 8 connectable with the above mentioned connector 5 so that, when the above mentioned connector 5 is connected to the above mentioned connector receptacle 8, the above mentioned electronic endoscope 1 will be connected to the above mentioned control apparatus 6. Further, a color monitor 7 as a displaying means is to be connected to the above mentioned control apparatus 6.

A rigid tip part 9 and a curvable part 10 curvable to the rear side and adjacent to this tip part 9 are provided in turn on the tip side of the above mentioned insertable part 2. When a curving operation knob 11 provided on the above mentioned operating part 3 is rotated, the above mentioned curvable part 10 will be able to be curved vertically and horizontally. Also, the above mentioned operating part 3 is provided with an inserting part 12 communicating with a forceps channel provided within the insertable part 2.

Figure 2:
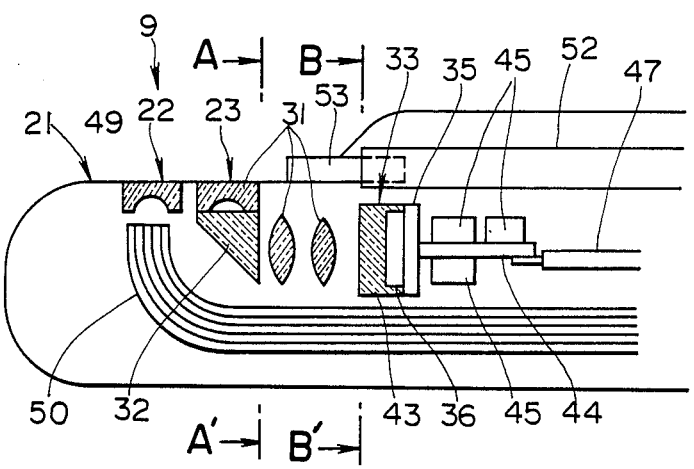
Figure 4:
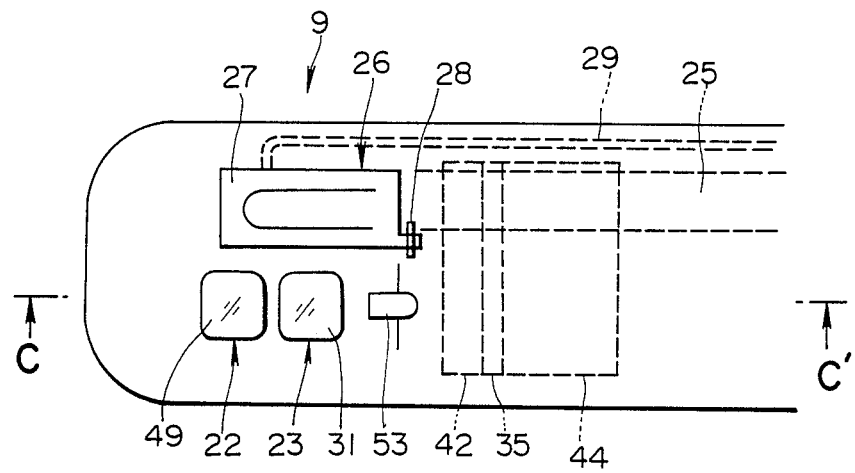

As shown in FIG. 2, the above mentioned tip part 9 has a plane part 21 formed by incising in the axial direction of the insertable part 2 the side part of a column spherical at the tip. On this plane part 21, as shown in FIG. 4, on one side, from the tip side, an illuminating window 22 and observing window 23 are provided in the axial direction of the insertable part 2. On the other side adjacent to the above mentioned illuminating window 22 and observing window 23, a forceps outlet 26 communicating with a forceps channel 25 is formed and a forceps raising stand 27 is arranged in this forceps outlet 26. This forceps raising stand 27 is rotatable with a rotary shaft 28 as a center and is rotated to the outer peripheral side by pulling a forceps raising wire 29 so as to be able to raise the tip side of the forceps inserted through the above mentioned forceps channel 25.

As shown in FIG. 2, the above mentioned observing window 23 is fitted with an objective lens system 31 with the visual field direction set on the side of the insertable part 2. A dach prism 32 bending the optical axis without inverting the image is interposed in this objective lens system 31 to bend the optical axis of the objective lens system 31 substantially at right angles with the base side of the insertable part 2. Therefore, the optical axis of this objective lens system 31 is substantially parallel with the axial direction of the above mentioned insertable part 2. In the image forming position of this objective lens system 31, a solid state imaging device (abbreviated as SID hereinafter) 33 is arranged to intersect substantially at right angles with the axial direction of the insertable part 2.

Figure 1:
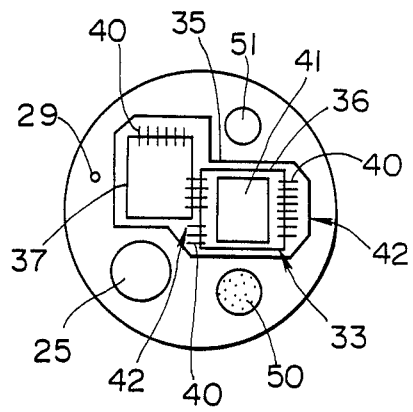
FIGS. 1 to 5 relate to the first embodiment of the present invention.

In this SID 33, a rectangular SID chip 36 is die-bonded on an SID substrate 35. In this embodiment, as shown in FIG. 1, the above mentioned SID substrate 35 is formed to be expanded to the left side of the SID chip 36 and a peripheral IC chip 37 is die-bonded on this expanded part. The above mentioned SID substrate 35 and SID chip 36; SID substrate 35 and peripheral IC chip 37; and SID chip 36 and peripheral IC chip 37 are respectively wire-bonded with bonding wires 40. The above mentioned SID chip 36 has a rectangular image area 41. In this embodiment, as shown in FIG. 1, in case the observing window 23 side is above, the wire bonding parts 42 for the above mentioned SID chip 36 will be provided on both right and left sides of the above mentioned image area 41.

The above mentioned SID chip 36 and peripheral IC chip 37 are wire-bonded and are then sealed on the entrance surface side with a transparent sealing resin 43.

On the back surface side of the above mentioned SID substrate 35, a peripheral substrate 44 fitted with peripheral electronic parts 45 is arranged in the axial direction of the insertable part 2 and both substrates 35 and 44 are connected with each other. Electrodes are formed on the back surface of the SID substrate 35 and the side surface of the peripheral substrate 44 connected with each other and are electrically connected. With the peripheral IC chip 37 on the above mentioned SID substrate 35 and the above mentioned peripheral electronic parts 45, the video output signal from the above mentioned SID 33 is amplified and the pulse driving the SID 33 is generated. A signal cable 47 transmitting and receiving signals between the above mentioned SID 33 and the signal processing circuit within the control apparatus 6 is connected to the rear end part of the above mentioned peripheral substrate 44, is inserted through the above mentioned insertable part 2 and universal cord 4 and is connected to the above mentioned connector 5.

On the other hand, the above mentioned illuminating window 22 is fitted with a light distributing lens 49. A light guide 50 of fibers is provided on the rear end side of this light distributing lens 49, is inserted through the above mentioned insertable part 2 and universal cord 4, is bent on the tip side to the above mentioned illuminating window 22 side, is opposed on the tip surface to the above mentioned light distributing lens 49 and is connected at the base end to the above mentioned connector 5. In this embodiment, as shown in FIG. 2, in case the observing window 24 side is above, the above mentioned light guide 50 of fibers will be inserted below the above mentioned SID 33.

As shown in FIG. 1, the above mentioned forceps channel 25 is provided below the above mentioned peripheral IC chip 37.

Also, as shown in FIG. 1, an air and water feeding tube 52 forming an air and water feeding channel 51 is inserted above the above mentioned SID 3 and is connected at the tip with an air and water feeding nozzle 53 arranged on the base side of the above mentioned observing window 23 and opening on this observing window 23 side as shown in FIG. 4.

Thus, in this embodiment, the observing window 23 is provided on the side of the tip part 9 and the SID 33 is arranged so as to intersect substantially at right angles with the axial direction of the insertable part 2 on the base side more than the observing window 23. The light guide 50 of fibers is inserted below (on the side reverse to the observing window 23) the above mentioned SID 33. The wire bonding parts 42 of the above mentioned SID 33 are provided on the sides different from the side on which the above mentioned light guide 50 of fibers is arranged, that is, on both right and left sides of the image area 41 of the SID chip 36.

If the above mentioned wire bonding part 42 is provided on the same side as the side on which the light guide 50 of fibers is arranged, that is, on the lower side, the light guide 50 of fibers will have to be moved downward by the space of this wire bonding part 42 and the tip part 9 will become that much thicker. If the outside diameter of the tip part 9 is not varied, the space for the above mentioned light guide 50 of fibers will become smaller, the number of fibers will become smaller and the visual field will become darker.

Figure 3:
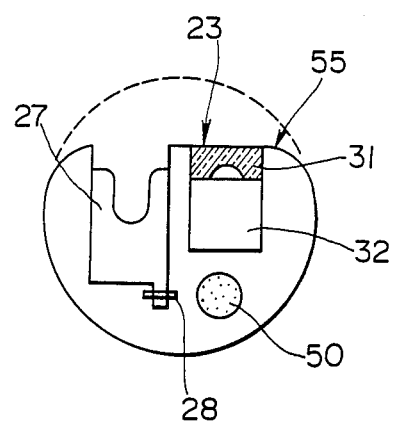

If the image area 41 of the SID chip 36 is moved upward by the space of the wire bonding part 42, the optical axis of the objective lens system 31 will also move upward, the position of the observing window 23 will also have to be moved upward, the tip part 9 will become thicker, the outer peripheral part 55 on the side of the observing window 23 in FIG. 3 will become sharper, the body wall or the like will be likely to be damaged, the illuminating window 22 and observing window 23 will have to be made smaller and such disadvantage as the deterioration of the optical characteristics will be produced.

According to this embodiment, as the above mentioned wire bonding part 42 is provided on the side different from the side on which the above mentioned light guide 50 of fibers is arranged, the tip part 9 will not become thicker as described above and can be made thinner.

Figure 6:
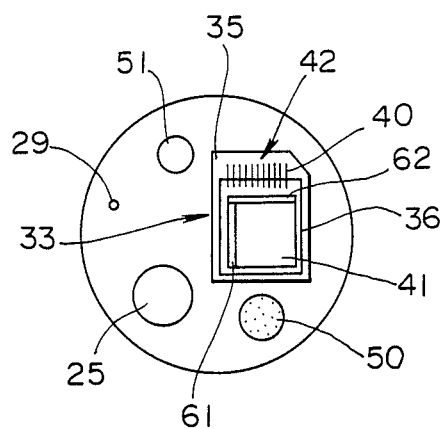
FIGS. 6 and 7 relate to the second embodiment of the present invention.
Figure 7:
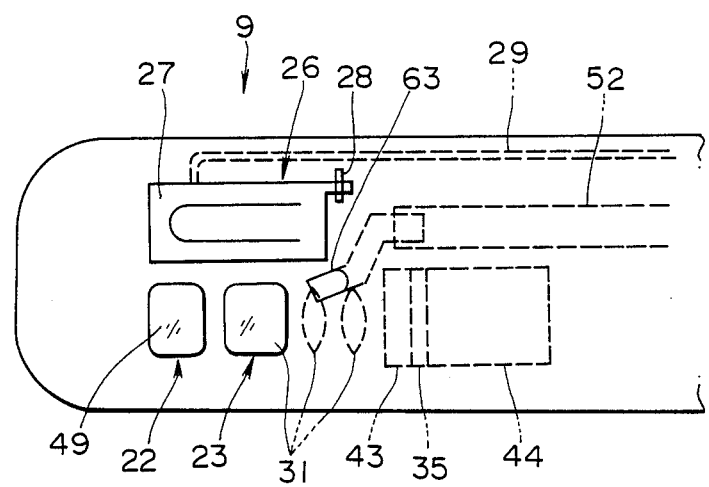

FIGS. 6 and 7 show the second embodiment of the present invention.

In this embodiment, as shown in FIG. 6 a bonding part 42 of an SID 33 consisting, for example, of 14 bonding wires 40 is provided on the side reverse to the light guide 50 of fibers, that is, on the upper side of the image area 41 to make the tip part 9 small in the diameter.

On the back surface of the SID substrate 35 on which an SID chip 36 is die-bonded, the same as in the first embodiment, electrodes are provided and are connected with a peripheral substrate 44.

By the way, in this embodiment, as shown in FIG. 6, in the above mentioned SID chip 36, an optical black row 61 is provided on the left side of the image area 41, a horizontal shift register 62 is provided on the upper side of the image area 41 and bonding wires 40 are provided on the upper side of this horizontal shift register 62. In such an arrangement, the transmitting direction is equal to that of an SID for general television cameras, therefore the same SID chip 36 and system as of general television cameras can be used and IC's for general television cameras can be used in various circuits within the control apparatus. Thus, this arrangement is adapted for the mass-production, can reduce the cost and is high in the expansibility of the system. Further, an IC or the like is not provided in the SID substrate 35 and the bonding wires 40 are provided along one side of the image area 41 to make this SID substrate 35 as small as possible. Therefore, this arrangement can be used also for straight viewing type and oblique viewing type endoscopes, is adapted for the mass-production and can reduce the cost.

Also, in this embodiment, the right upper corner of the above mentioned SID substrate 35 is chamfered to reduce the outer peripheral projection and to make the diameter small.

Also, in this embodiment, the air and water feeding tube 52 forming the air and water feeding channel 51 is inserted above the forceps channel 25 so as not to overlap with the SID 33, the diameter is made smaller and, as shown in FIG. 7, an air and water feeding nozzle 63 is bent to be like S and the tip side is directed to the observing window 23 side.

The other formations, operations and effects are the same as in the first embodiment.

By the way, in the above mentioned first and second embodiments, the visual field direction is not limited to be of the side viewing intersecting at right angles with the axial direction of the insertable part 2 but may be of the side forward oblique viewing and side rearward oblique viewing.

FIGS. 8 to 12 show the third embodiment of the present invention.

Figure 11:
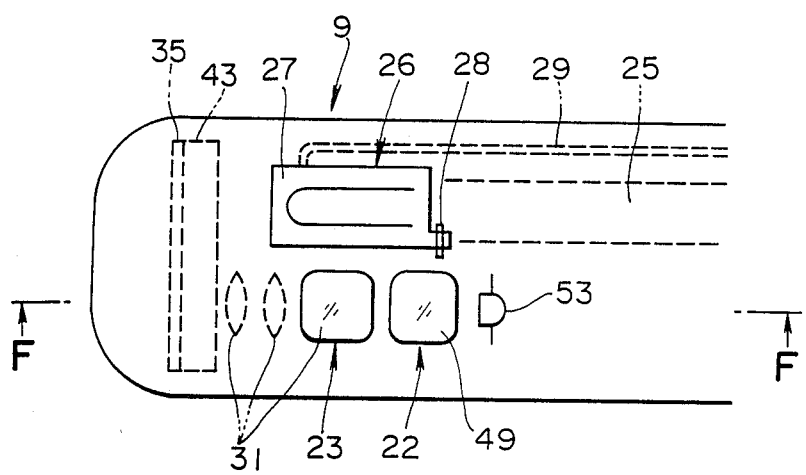

In this embodiment, on the plane part 21 of the tip part 9, as shown in FIG. 11, on one side, from the tip side, an observing window 23 and illuminating window 22 are provided in the axial direction of the insertable part 2. On the other side adjacent to the above mentioned observing window 23 and illuminating window 22, a forceps outlet 26 communicating with a forceps channel 25 is formed and is provided with a forceps raising stand 27 rotatable with a rotary shaft 28 as a center. When a forceps raising wire 29 is pulled, this forceps raising stand 27 will rotate to the outer peripheral side so as to be able to raise the tip side of the forceps inserted through the above mentioned forceps channel 25.

Figure 9:
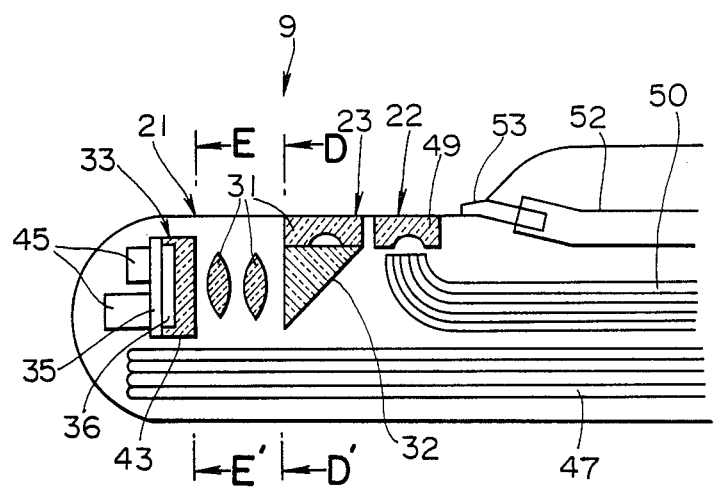

The above mentioned illuminating window 22 is fitted with a light distributing lens 49. A light guide 50 of fibers is provided on the rear end side of this light distributing lens 49 and is inserted through the insertable part 2 and universal cord 4. In this light guide 50 of fibers, on the tip side, the tip surface bent to the above mentioned illuminating window 22 side is opposed to the above mentioned light distributing lens 45 and, at the base end, the light guide is connected to a connector 5. In this embodiment, as shown in FIG. 9, the above mentioned light guide 50 of fibers is inserted substantially through the center of the vertical direction of the insertable part 2.

The above mentioned observing window 23 is fitted with an objective lens system 31 in which the visual field direction is set on the side of the insertable part 2. A dach prism 32 bending the optical axis without inverting the image is interposed in this objective lens system 31 to bend the optical axis of the objective lens system 31 substantially at right angles with the tip side of the insertable part 2. Therefore, the optical axis of this objective lens system 31 is substantially parallel with the axial direction of the above mentioned insertable part 2 and the SID 33 is arranged in the image forming position of this objective lens system 31 so as to intersect substantially at right angles with the axial direction of the insertable part 2.

Figure 8:
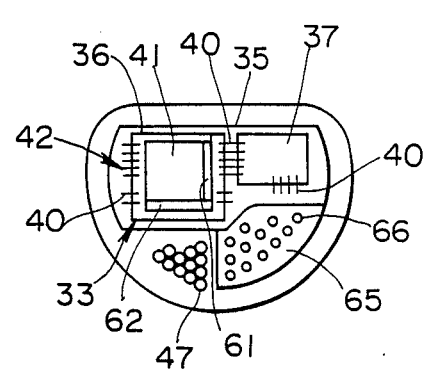
FIGS. 8 to 12 relate to the third embodiment of the present invention.
Figure 10:
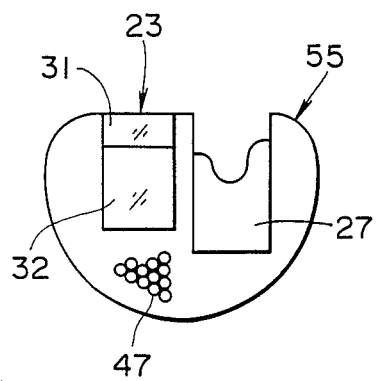

A rectangular SID chip 36 is die-bonded on a substrate 35 in this SID 33. In this embodiment, as shown in FIG. 8, the above mentioned substrate 35 is formed to be expanded to the right side (as seen from the imaging surface side) of the SID chip 36 and a peripheral IC chip 37, for example, for shaping driving pulses is die-bonded on this expanded part. The above mentioned substrate 35 and SID chip 36; substrate 35 and peripheral IC chip 37; and SID chip 36 and peripheral IC chip 37 are respectively wire-bonded with bonding wires 40. The above mentioned SID chip 36 has a rectangular image area 41. In this embodiment, the bounding wires 40 connected to the above mentioned SID chip 36 are 14 wires which are provided as distributed on the right and left of the above mentioned image area 41 in case the observing window 23 side is above as shown in FIG. 8.

By the way, in this embodiment, as shown in FIG. 8, the above mentioned SID chip 36 is provided with an optical black row 61 on the right side of the image area 41 and with a horizontal shift register 62 on the lower side of the image area 41. In such arrangement, the vertical transmitting direction is downward in FIG. 8 and the horizontal transmitting direction is leftward. These transmitting directions are equal to those of an SID for general television cameras. Therefore, the same SID chip 36 and system as of general television cameras can be used and an IC for general television cameras can be used for various circuits within the control apparatus 6. Thus, this arrangement is adapted for the mass-production, can reduce the cost and improves the expansibility of the system.

The above mentioned SID chip 36 and peripheral IC chip 37 are wirebonded and are then sealed with a sealing resin 43 on the entrance surface side.

Peripheral electronic parts 45 are fitted on the back surface side of the above mentioned substrate 35. With the peripheral IC chip o the above mentioned substrate 35 and the above mentioned peripheral electronic parts 45, the video output signal from the above mentioned SID 33 is amplified and the pulse driving the SID 33 is generated.

As shown in FIG. 8, a signal cable connecting substrate 65 is provided below the peripheral IC chip 37 in the above mentioned substrate 35 and, for example, 12 signal cables 47 are connected to signal cable connecting parts 66 provided in this signal cable connecting substrate 65. That is to say, the core wires of the signal cables 47 pass through the above mentioned signal cable connecting substrate 65. These signal cables 47 are inserted through the above mentioned insertable part 2 and universal cord 4, are connected on the base end side to the connector 5, pass on the tip side below the above mentioned SID 33 as shown in FIGS. 8 and 9, bend to the right side near the tip within the tip part 9, further bend to the base side and are connected to the above mentioned signal cable connecting part 65.

Figure 12:
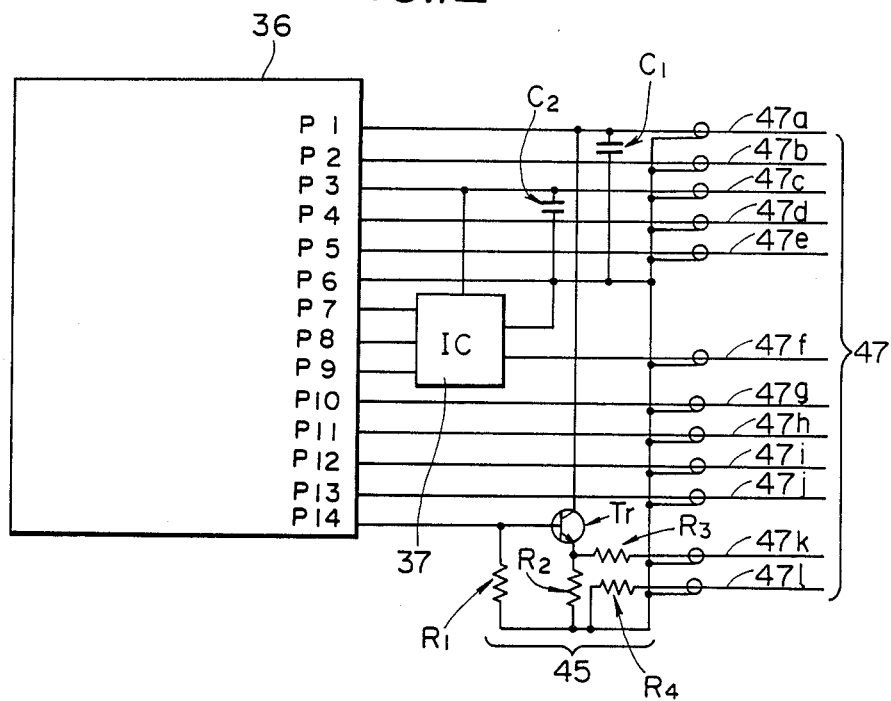

By the way, the above mentioned SID chip 36 is of such terminal formation as is shown, for example, in FIG. 12. That is to say, the SID chip 36 is provided with 14 terminals of a current source (Vcc) terminal P1, output load transistor load gate (LG) terminal P2, output gate (OG) terminal P3, protecting P well (PT) terminal P4, substrate bias (Sub) terminal P5, ground (GND) terminal P6, reset pulse ($\phi R$) terminal P7, horizontal register clock ($\phi H1$ and H2) terminals P8 and P9, vertical register clock terminals ($\phi V1$, $\phi V2$, $\phi V3$ and $\phi V4$) P10, P11, P12 and P13 and video output (V0) terminal P14.

A direct current voltage is applied to the current source terminal P1 by a cable 47a. A load gate bias voltage, output gate bias voltage and protecting well bias voltage are respectively applied to the output load transistor load gate terminal P2, output gate terminal P3 and protecting P well terminal P4 by cables 47b, 47c, 47d and 47e. The driving pulse shaping IC 37 is connected to the reset pulse terminal P7 and horizontal register clock terminals P8 and P9. This IC 37 shapes clock pulses fed by a cable 47f and applies a reset pulse $\phi R$ and horizontal register clock pulses $\phi H1$ and $\phi H2$ to the respective terminals P7, P8 and P9. Vertical register clock pulses $\phi V1$, $\phi V2$, $\phi V3$ and $\phi V4$ are respectively applied to the vertical register clock terminals P10, P11, P12 and P13 by cables 47g, 47h, 47i and 47j. An emitter follower circuit formed of a transistor Tr and resistances R1, R2, R3 and R4 as a peripheral electronic circuit 45 is connected to the video output terminal P14 so that the output signal of the SID 36 may be led out through a cable 47k by converting (matching) the impedance. By the way, the above mentioned cable 47k is provided as paired with a noise canceling dummy cable 47l. The shielding wires of the above mentioned respective cables 47a to 47l and the IC 37 are connected to the ground terminal P6 and are ground. The current source cable 47a and output gate cable 47c are connected to the above mentioned ground terminal P6 through condensers C1 and C2 and are grounded by an alternating current.

As shown in FIG. 9, an air and water feeding tube 52 forming an air and water feeding channel 51 is inserted above the above mentioned light guide 50 of fibers and is connected at the tip with an air and water feeding nozzle 53 arranged on the base side of the above mentioned illuminating window 23 and opening on this illuminating window 23 side.

Thus, in this embodiment, the observing window 23 is provided on the side of the tip part 9 and the SID 33 is arranged so as to intersect substantially at right angles with the axial direction of the insertable part 2 on the tip side more than this observing window 23. The signal cables 47 are inserted below (on the side reverse to the observing window 23) the above mentioned SID 33. The wire bonding part 42 of the above mentioned SID 33 is provided on the side different from the side on which the above mentioned signal cables 47 are arranged, that is, on each of both right and left sides of the imaging area 41 of the SID chip 36.

If the above mentioned wire bonding part 42 is provided on the same side as the side on which the above mentioned signal cables 47 are arranged, that is, on the lower side, the signal cables 47 will have to be moved downward by the space of this wire bonding part 42 and the tip part 9 will become that much thicker. Also, if the image area 41 of the SID chip 36 is moved upward by the space of the wire bonding part 42, there will be disadvantages that the optical axis of the objective lens system 31 will also move upward, the position of the observing window 23 will have to be also moved upward, the tip part 9 will become thicker, the outer peripheral part 55 on the side of the observing window 23 in FIG. 10 will become so sharp as to be likely to hurt the body wall or the like, the illuminating window 22 and observing window 23 will have to be made smaller and the optical characteristics will deteriorate.

According to this embodiment, as the above mentioned wire bonding part 42 is provided on the side different from the side on which the above mentioned signal cables 47 are arranged, the tip part 9 will not become thicker as described above and can be made small in the diameter.

Figure 13:
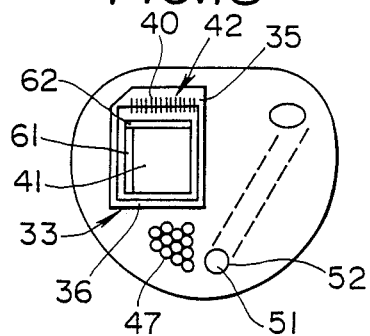
FIGS. 13 to 15 relate to the fourth embodiment of the present invention.
Figure 14:
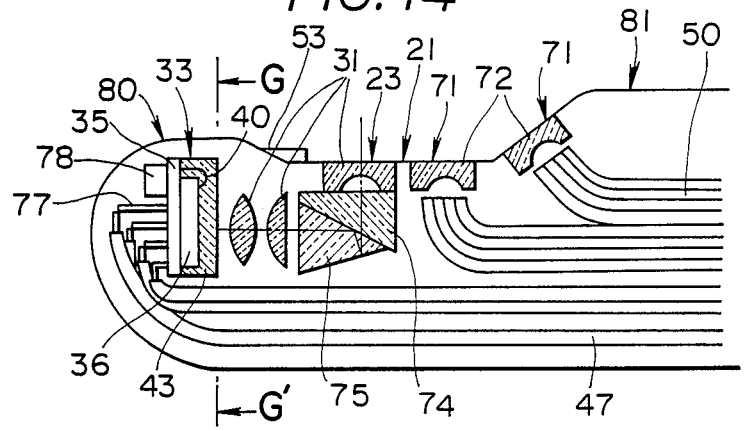
Figure 15:
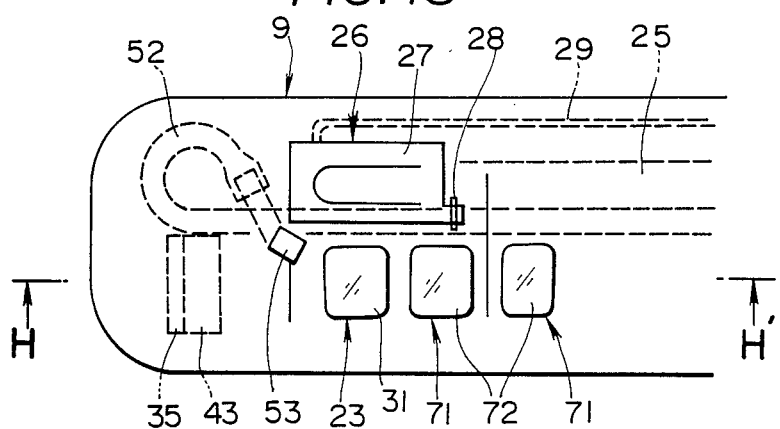
Figure 16:
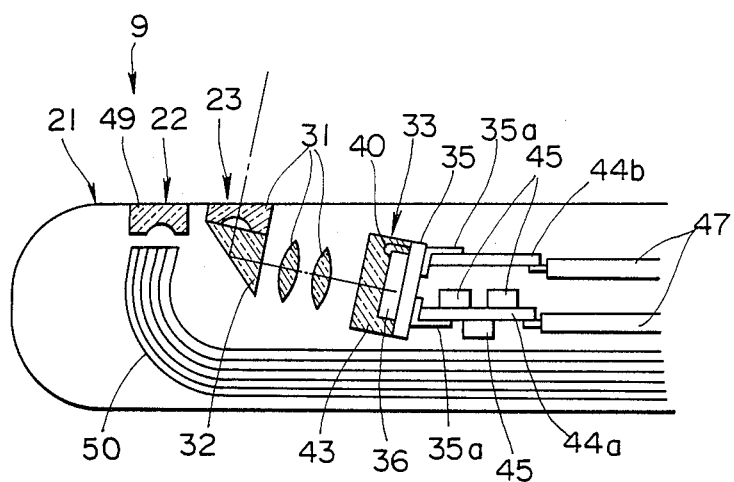
FIGS. 16 to 23 relate to the fifth embodiment of the present invention.

FIGS. 13 to 15 show the fourth embodiment of the present invention.

In this embodiment, as shown in FIGS. 14 and 15, on the plane part 21 of the tip part 9, from the tip side an observing window 23 and illuminating window 71 are provided in the axial direction of the insertable part 2 and further an illuminating window 71 is provided also on the slope on the base side of the above mentioned illuminating window 71.

The light guide 50 of fibers is forked on the tip side into two branches arranged so as to be opposed respectively to light distributing lenses 72 fitted respectively to the above mentioned illuminating windows 71. An object to be imaged is to be illuminated from the two illuminating windows.

The optical axis of the objective lens system 31 is bent substantially at right angles with the tip side of the insertable part 2 by a twice reflecting prism consisting of two prisms 74 and 75 so that the image will not be inverted vertically but will be inverted horizontally. An SID 33 is arranged in the image forming position of the above mentioned objective lens system 31.

On the tip side of the plane part 21 of the tip part 9, a projecting part 80 is formed to project somewhat on the outer peripheral side from the plane part 21. The above mentioned SID 33 and an air and water feeding nozzle 53 opposed from the tip side to the above mentioned observing window 23 are contained within this projecting part 80. By the way, as shown in FIG. 14, the height (projection in the outer peripheral direction) of the above mentioned projecting part 80 is so lower than a column part 81 of the tip part 9 and the curvature is so large that the degree of the increase of the pain given to the patient is low.

As shown in FIG. 13, the SID chip 36 of the above mentioned SID 33 is provided with an optical black row 61 on the left side of the image area 41 and with a horizontal shift register 62 on the upper side of the image area 41. In such an arrangement, in FIG. 13, the vertical transmitting direction is upward and the horizontal transmitting direction is rightward. These are equal to the transmitting directions of an SID for general television cameras. Therefore, the same as in the above mentioned third embodiment, the same SID chip 36 and system as of general television cameras can be used.

In this embodiment, as shown in FIG. 13, the wire-bonding part 42 of the SID 33 is provided on the side reverse to the signal cables 47, that is, on the upper side of the image area 41 to make it possible to make the tip part 9 small in the diameter. As the bonding wires 40 are provided along the above mentioned horizontal shift register 62, the arrangement of the wiring in the SID chip 36 can be simplified.

Also as the bonding wires 40 are provided along one side of the image area 41, the substrate 35 can be made smallest. Further, the left upper corner in FIG. 13 of the substrate 35 is chamfered to reduce the projection in the outer peripheral direction and to make the diameter smaller. The substrate 35 is thus made so small as to be able to be used for straight viewing type and oblique viewing type endoscopes, to be adapted for the mass-production and to be able to reduce the cost.

On the back surface of the above mentioned substrate 35, external leads 77 of sequentially varied lengths are provided and are connected with the signal cables 47. By the way, the peripheral electronic part 78 in FIG. 14 is one chip as made of the peripheral IC chip 37 and peripheral electronic part 45 in the third embodiment. A part of the condenser and resistance is formed within the above mentioned substrate 35.

An air and water feeding tube 52 is inserted below the middle of the right and left as shown in FIG. 13, is bent on the tip side to the right upper side near the tip within the tip part 9 as shown in FIG. 15, is further bent to the base side and is connected to the air and water feeding nozzle 53 arranged on the tip side of the above mentioned observing window 23. This air and water feeding nozzle 53 is opposed to the observing window 23 from the tip side, is shorter in the distance between the air and water feeding nozzle 53 and observing window 23 than in the third embodiment, is therefore high in the washing force and is good in separating water.

By the way, in FIG. 13, the left upper corner of the substrate is chamfered. However, it is needless to say that, in case the forceps raising stand 27 is arranged on the left side of the SID 33, the right upper corner had better be chamfered. Thus, fitting the same SID chip 36 to the substrate 35 in response to the kind of the endoscope is much easier than making n exclusive SID chip 36 and also the imaging apparatus 6 can be commonly used. In such case, as in this embodiment, the bonding wires 40 made in one row can be easily arranged in any endoscope.

The other formations, operations and effects are the same as in the third embodiment.

By the way, in the above mentioned third and fourth embodiments, the visual field direction is not limited to the side viewing intersecting at right angles with the axial direction of the insertable part 2 but may be a side forward oblique viewing or side rearward oblique viewing.

FIGS. 16 to 23 show the fifth embodiment of the present invention.

In this embodiment, the optical axis of the objective lens system 31 is provided as inclined to the axial direction of the insertable part 2 and further the SID substrate 35 is provided with two substrates 44a and 44b.

The observing window 23 provided in the tip part 9 is fitted with the objective lens system 31 in which the visual field direction is set obliquely rearward on the side of the insertable part 2. A dach prism 32 refracting the optical axis without inverting the image is interposed in this objective lens system 31 to bend the optical axis of the objective lens system 31 substantially at right angles so as to be directed to the axial direction center of the insertable part 2 on the base side of the insertable part 2. Therefore, the optical axis of this objective lens system 31 inclines to the axial direction of the above mentioned insertable part 2 and the SID 33 as an imaging means is arranged as inclined to the axial direction of the insertable part 2 in the image forming position of this objective lens system 31.

In this SID 33, a rectangular SID chip 36 is diebonded on an SID substrate 35. In this embodiment, the same as is shown in the second and fourth embodiments, the upper side of the SID chip 36 and the upper side of the SID substrate 35 are wire-bonded by the boding wires 40.

On the back surface side of the above mentioned SID substrate 35, the first peripheral substrate 44a fitted with the peripheral electronic parts 45 and the second peripheral substrate 44a are connected so as to be arranged in the axial direction of the insertable part 2 through leads 35a. Signal cables 47 transmitting and receiving signals between the above mentioned SID 33 and the signal processing circuit within the control apparatus 6 are connected to the rear ends of the above mentioned first peripheral substrate 44a and second peripheral substrate 44b, are inserted through the above mentioned insertable part 2 and universal cord and are connected to the above mentioned connector 5.

On the other hand, the illuminating window 22 provided in front of the above mentioned observing window is fitted with a light distributing lens 49 on the rear end side of which the light guide 50 of fibers is provided so as to be able to illuminate the visual field direction of the objective lens system 31.

Figure 17:
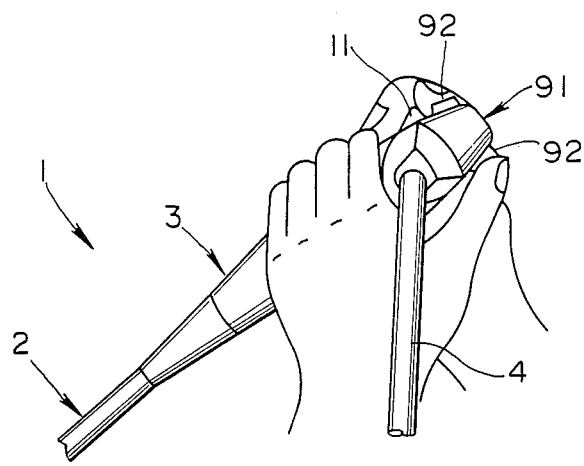
Figure 18:
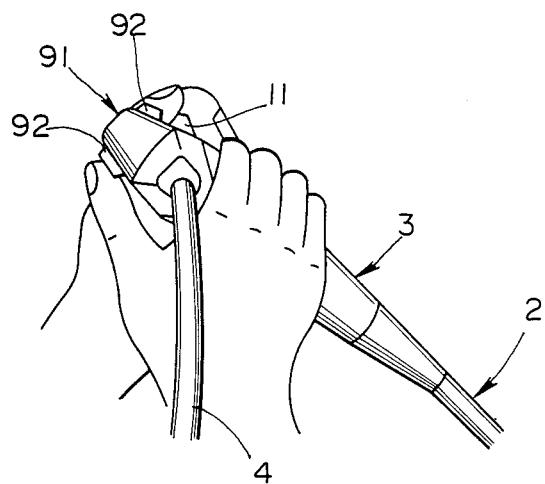
Figure 19:
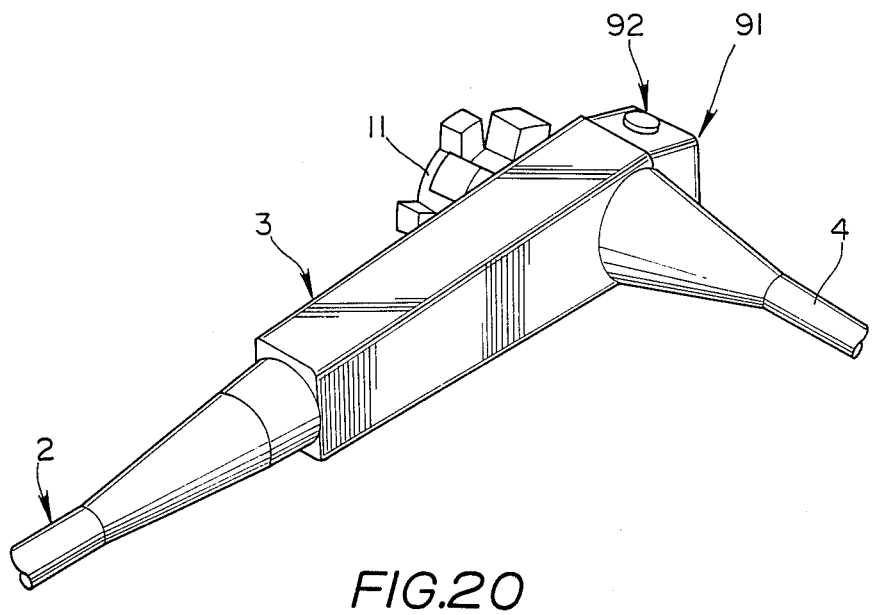
Figure 20:
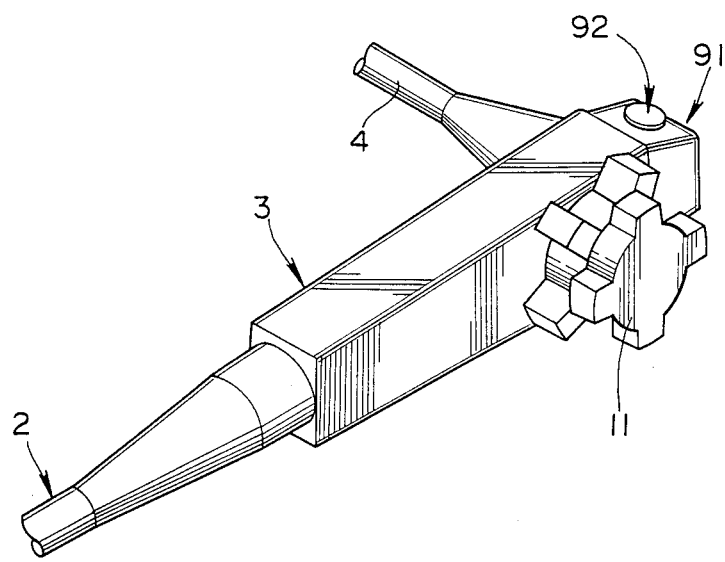
Figure 21:
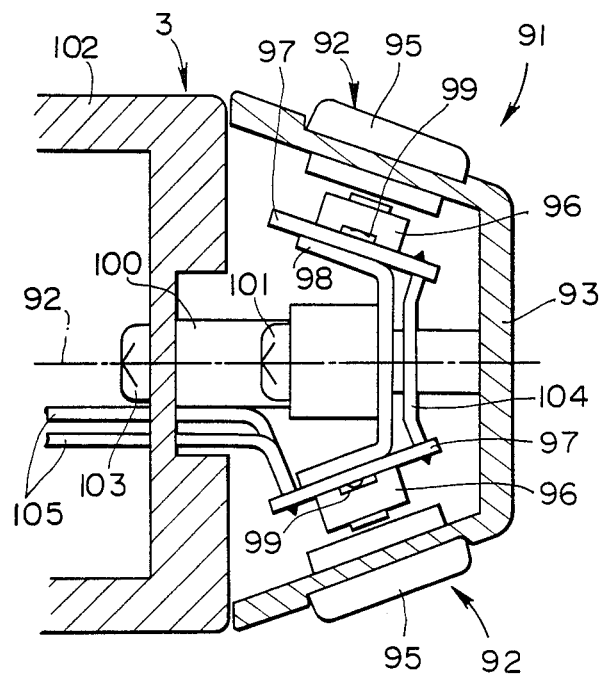

Also, in this embodiment, as in FIGS. 17 to 21, a switch part 91 is provided in the rear of the above mentioned operating part 3 and is provided with a pair of push button type switches 92 having the function of the above mentioned control apparatus 6 or peripheral device, for example, the same operation of controlling a freezing or VTR picture recording in substantially symmetrical positions with respect to the center axis of the above mentioned operating part 3 on the side different from the side of the above mentioned curving operation knob 11. The above mentioned switch part 91 is provided with a cover 93 fitted with key tops 95 of a pair of switches 92 in substantially symmetrical positions with respect to the center 94 of the above mentioned operating part 3 on the side different from the side of the curving operation knob 11 of the operating part 3 as shown in FIGS. 19 and 20. Push button type switch bodies 96 are arranged as opposed to the above mentioned key tops 95 within the above mentioned cover 93 and are fitted, for example, by soldering respectively to the substrates 97 which are fixed by screws 99 to a plate-like fixing member 98 bent in response to the contour of the cover 93. The above mentioned fixing member 98 is fastened together with a receiving member 100 to the above mentioned cover 93 by a screw 101. Further, the above mentioned receiving member 100 is fitted to the operating part body 102 by a screw 103.

For example, two lead wires 104 are provided between both substrates 97. The pair of switch bodies 96 are electrically parallelly connected through these lead wires 104. For example, two lead wires 105 electrically connected to the above mentioned switch bodies 96 are connected to one substrate 97, are inserted through the universal cord 4 together with the above mentioned signal cable 47 and light guide 50 of fibers through the operating part 3 and are connected to the above mentioned connector 5. By connecting this connector 5 to the connector receptacle 8 of the above mentioned control apparatus 6, the above mentioned switch bodies 96 are connected to the signal processing circuit within the above mentioned control apparatus 6 and to the peripheral devices. When at least one of the key tops 95 eposed on the cover 93 side of the above mentioned switch part 91 is pressed and operated, at least one of the switch bodies 96 will operate to be on and off to control the function of the above mentioned control apparatus 6 or peripheral device, for example, the freezing or VTR picture recording.

The operating method of the above mentioned switch part 91 shall be explained with reference to FIGS. 17 and 18.

FIG. 17 shows the operating part 3 as held with a left hand. FIG. 18 shows it as held with a right hand. As shown in these drawings, in this embodiment, as a pair of equivalent switches 92 are provided in substantially symmetrical positions with respect to the center axis of the operating part 3, when the operating part 3 is held with either of the right and left hands, one of the above mentioned switches 92 will be in the position in which it is operatable with (for example, the thumb of) the hand holding the operating part 3. Therefore, the switch 92 can be easily operated with the hand holding the operating part 3 and the function of the above mentioned control apparatus 6 or peripheral device can be controlled.

Figure 22:
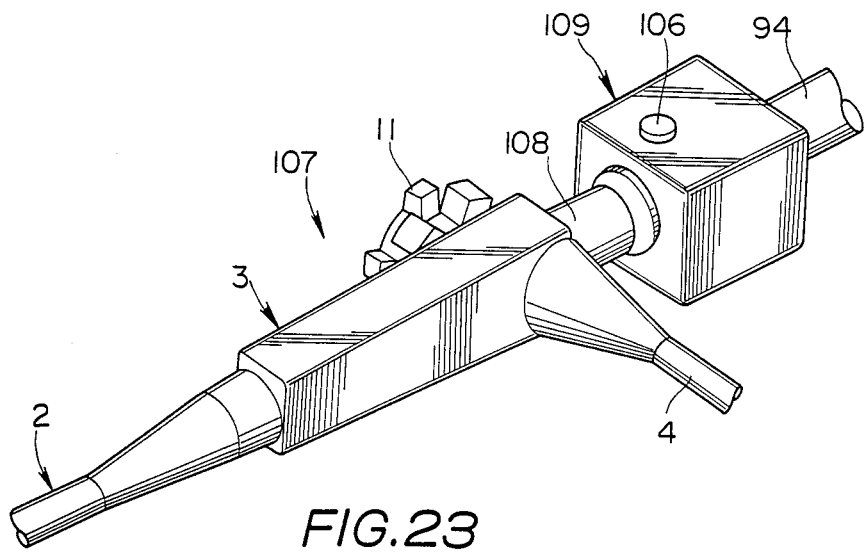
Figure 23:
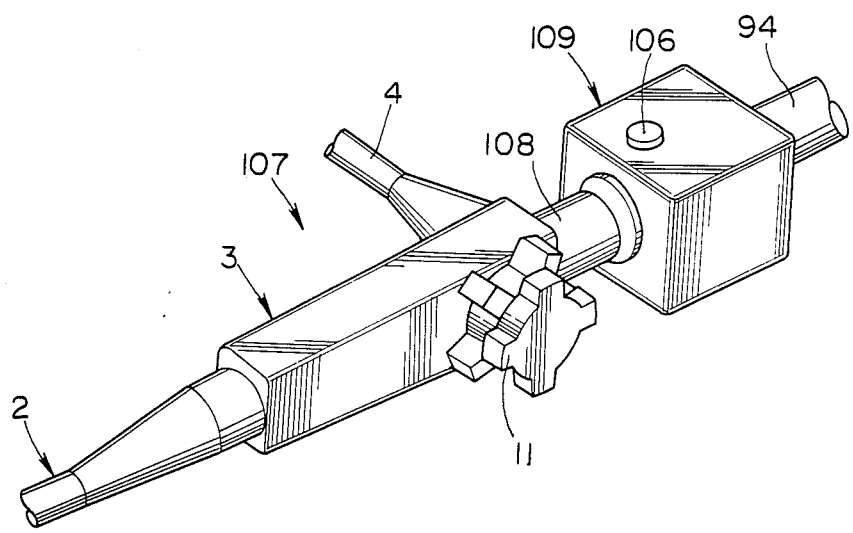

Also, as shown in FIGS. 22 and 23, a pair of switches 106 operating the same to control the function of the control apparatus 6 or peripheral device may be provided in an externally fitted television camera 109 fitted to the eyepiece part 108 of a fiber scope 107 with which a naked eye observation is possible.

In the above mentioned fiber scope 107, an image guide of fibers not illustrated is inserted through the insertable part 2 and the tip surface of this image guide of fibers is arranged in the image forming position of the objective lens system 31. The object image formed by the above mentioned objective lens system 31 is transmitted to the operating part 3 by the above mentioned image guide of fibers and can be observed with the eyepiece part 108 provided at the rear end of this operating part 3. The television camera 109 can be connected to this eyepiece part 108. This television camera 109 is connected, for example, to the control apparatus 6 through a signal cable 110 and the object image imaged by the above mentioned television camera 109 can be displayed in the color monitor 7 or can be recorded in a VTR.

In this embodiment, in the above mentioned television camera 109, a pair of switches 106 operating the same to control the function of this television 109, the above mentioned control apparatus 6 or peripheral device are provided in substantially symmetrical positions with respect to the center axis of the above mentioned operating part 3 on the side different from the side on which the curving operation knob of the operating part 3 is provided.

When the switches 106 are provided as mentioned above, even if the operating part 3 of the fiber scope 107 is helf with either of the right and left hands, one of the switches 106 of the above mentioned television camera 109 will be able to be in the position in which the switch is operatable with (for example, the thumb of) the hand holding the operating part. Therefore, the switch 106 can be easily operated with the hand holding the operating part 3 and the function of the above mentioned television camera 109, control apparatus or peripheral device can be controlled.

By the way, in case it is necessary to operate the functions of two or more of the control apparatus 6 and peripheral devices with the hand holding the operating part 3, a pair of equivalent switches for the respective functions may be provided in substantially symmetrical positions with respect to the center axis of the operating part 3.

The switches may be at least a pair for each function or, for example, three may be provided.

The controlling means is not limited to the switch but such continuous control as a sliding type or rotary type resistance may be used.

The other formations are the same as in the first embodiment.

In this embodiment, when the substrate provided on the back surface side of the SID substrate 35 is divided into two parts, the length of the substrate can be made short and the length of the tip part 9 can be made short. The other effects are the same as in the third embodiment.

By the way, the present invention is not limited to the above mentioned respective embodiments. For example, the bonding wire part 42 may be provided on one of the right and left sides of the image area, on one of the right and left sides and the upper side or on both right and left sides and the upper side.

The contents arranged on the opposite observing window side are not limited to the light guide 50 of fibers and signal cable 47 but may be a forceps channel and air and water feeding channel.

Also, a synchronous system provided with a filter array in which color filters transmitting respectively three colors of R, G and B of an illuminating light are arranged in the form of a mosaic may be arranged.

In the present invention, it is apparent that different working modes in a wide range can be formed on the basis of the present invention without departing from the spirit and scope of the invention. The present invention is not restricted by its specific working modes except being limited by the appended claims.

What is claimed is:

1. An electronic endoscope having a solid state imaging device, comprising:
    an insertable part extended from an operating part and having an observing window on the side of a tip part;
    a solid state imaging device for receiving an incident light from said observing window and arranged so as to intersect substantially at right angles with the axial direction of said insertable part, wherein said solid state imaging device is formed of a substrate and a solid state imaging chip secured to said substrate;
    a plurality of internal members having signal line means electrically connected to said substrate, wherein one of said plurality of internal members is arranged of an opposite observing window side of said solid state imaging chip in a plane including said solid state imaging device; and
    a wire bond part which electrically connects said solid state imaging chip with said substrate and is provided on a side different from the side of said plurality of internal members.

2. An electronic endoscope according to claim 1, wherein said wire bonding parts consist of a chip side wire bonding parts provided on said solid state imaging chip and substrate side wire bonding parts provided on said substrate.

3. An electronic endoscope according to claim 1 wherein at least one of said plurality of internal members is a light guide fiber means for transmitting an illuminating light.

4. An electronic endoscope according to claim 1 wherein at least one of said plurality of internal members is a signal line means for inputting and outputting electric signals into and out of said solid state imaging device.

5. An electronic endoscope according to claim 1 wherein at least one of said plurality of internal members is a forceps channel.

6. An electronic endoscope according to claim 1 wherein said endoscope includes an objective lens system and wherein a part of the optical axis of said objective lens system forms an image on a receiving light face of said solid state imaging device and said solid state imaging device inclines towards the axial direction of the insertable part.

7. An electronic endoscope according to claim 1, wherein said bonding part is provided at a position on the right and left side portions of said solid state imaging device.

8. An electronic endoscope according to claim 7, wherein said wire bonding part is wire-bonded on one side with a peripheral IC chip.

9. An electronic endoscope according to claim 1, wherein said wire bonding part is at least partially chamfered.

10. An electronic endoscope according to claim 1, wherein the imaging surface of said solid state imaging device is directed to the base side portion of the insertable part and said signal line means is one of said plurality of internal members and is connected to the opposite side of said imaging surface of said solid state imaging device.

* * * * *